United States Patent [19]

Wu et al.

[11] 4,255,596

[45] Mar. 10, 1981

[54] PREPARATION OF ETHYLENE GLYCOL FROM ETHYLENE

[75] Inventors: Ching-Yong Wu, Fox Chapel Borough; Thaddeus P. Kobylinski, Gibsonia; John E. Bozik, Plum Borough, all of Pa.

[73] Assignee: Gulf Research & Development Company, Pittsburgh, Pa.

[21] Appl. No.: 124,416

[22] Filed: Feb. 25, 1980

Related U.S. Application Data

[63] Continuation-in-part of Ser. No. 948,243, Oct. 3, 1978, abandoned.

[51] Int. Cl.³ .............................................. C07C 29/04
[52] U.S. Cl. .................................. 568/860; 568/311; 568/815
[58] Field of Search ........................................ 568/860

[56] References Cited

U.S. PATENT DOCUMENTS

| | | | |
|---|---|---|---|
| 2,575,403 | 11/1951 | Young et al. | 568/814 |
| 2,867,666 | 1/1959 | Erickson et al. | 568/815 |
| 3,351,635 | 11/1967 | Kollar | 568/815 |
| 3,526,674 | 9/1970 | Becker et al. | 585/437 |
| 3,665,047 | 5/1972 | Gislon et al. | 568/715 |
| 3,822,321 | 7/1974 | Maurin et al. | 568/860 |
| 3,860,662 | 1/1975 | Kollar | 568/815 |
| 4,049,724 | 9/1977 | Sheng et al. | 568/860 |

OTHER PUBLICATIONS

Sharpless et al., "J. Am. Chem. Soc.", 98:7 (Mar. 31, 1976), pp. 1986–1987.

*Primary Examiner*—Joseph E. Evans

[57] ABSTRACT

Ethylene is converted to ethylene glycol at high selectivity in a process in which ethylbenzene hydroperoxide and water are reacted with ethylene in the presence of osmium tetroxide catalyst and a base at a pH of about 14.

8 Claims, No Drawings

PREPARATION OF ETHYLENE GLYCOL FROM ETHYLENE

This application is a continuation-in-part of United States Ser. No. 948,243, filed Oct. 3, 1978, now abandoned.

SUMMARY OF THE INVENTION

This invention relates to a procedure for reacting ethylene with ethylbenzene hydroperoxide to produce ethylene glycol at high selectivity.

We have discovered a process by which ethylene can be converted to ethylene glycol at an overall selectivity of 95 percent or higher. In our procedure a solution of ethylbenzene hydroperoxide in ethylbenzene and an organic polar solvent together with a small amount of a tetraalkylammonium hydroxide and osmium tetroxide is pressured with ethylene. The product mixture contains ethylene glycol with no identifiable amount of acetaldehyde, acetic acid, ethanol, acetals of acetaldehyde, glycolaldehyde or glycolic acid being present.

DESCRIPTION OF THE INVENTION

Ethylene glycol is currently produced commercially in a multistage process from ethylene at an overall selectivity of about 50 to 65 percent. In the first step ethylene is oxidized to ethylene oxide at elevated temperature and pressure using oxygen and a silver-containing catalyst. The reaction requires very careful control of operating conditions to obtain a selectivity as high as 70 percent. Generally, at least about one-third of the ethylene is lost as carbon dioxide. The ethylene oxide is then hydrated either catalytically using a dilute aqueous solution of a strong acid or at high temperatures and pressures, with some diethylene and triethylene glycols being formed as by-products.

U.S. Pat. No. 4,049,724 describes the preparation of glycols from alkenes and from unsaturated alcohols in an aqueous system using osmium tetroxide and specifying stable and water-soluble aliphatic hydroperoxides such as tert-butyl hydroperoxide while a critical pH of 8 to 12 is maintained by a suitable combination of alkali metal buffering compounds. Ethylbenzene hydroperoxide, which is relatively unstable and is not water soluble or aliphatic, is not specified. The preparation of propylene glycol utilizing tert-butyl hydroperoxide is exemplified in the patent at a selectivity based on the hydroperoxide at 45 percent. When this reaction was attempted by us using ethylbenzene hydroperoxide in place of the tert-butyl hydroperoxide, a selectivity based on the hydroperoxide of only 2.3 percent to propylene glycol resulted.

Sharpless et al, JACS, 98:7, pages 1968–1987 report the preparation of the diol of 1-decene at a yield of only 73 percent based on the 1-decene. The ketol of 1-decene is specified to be a major by-product of this reaction. The production of such ketols has been a persistent problem in efforts to convert olefins to diols. Sharpless et al utilize 60 percent excess tert-butyl hydroperoxide in a tert-butyl alcohol solution containing tetraethylammonium hydroperoxide, water and osmium tetroxide catalyst. The selectivity of the diol of 1-decene based on the tert-butyl hydroperoxide was only 46 percent. When this procedure was repeated by us using ethylbenzene hydroperoxide instead of tert-butyl hydroperoxide, the yield of the diol of 1-decene based on the 1-decene diminished to 24.8 percent with the selectivity based on the ethylbenzene hydroperoxide being a trivial 15.5 percent.

Ethylene is well recognized to be relatively unreactive including unreactive to oxidation, as pointed out in U.S. Pat. No. 4,046,782. For example, Swern, JACS 69, 1692 (1974) demonstrates with data that ethylene is only one-twenty fifth as reactive to oxidation with peracids as 1-decene. Furthermore, ethylbenzene hydroperoxide at a concentration of 40 percent in ethylbenzene is unstable at room temperature (20°–25° C.).

Notwithstanding this highly negative information regarding both ethylene and ethylbenzene hydroperoxide, we have surprisingly discovered that ethylbenzene hydroperoxide and a stoichiometric excess, preferably at least about a 25 percent excess, of ethylene readily react in an ethylbenzene-polar solvent containing a tetraalkylammonium hydroxide and osmium tetroxide to form ethylene glycol at a selectivity based on ethylene of greater than 95 percent and greater than 70 percent based on the ethylbenzene hydroperoxide. These exceptional and unexpected results are further emphasized by the surprising discovery that no other ethylene derivative, such as acetaldehyde, acetic acid, ethanol, acetals of acetaldehyde, glycoladehyde or glycolic acid, has been identified in the reaction product.

Ethylbenzene hydroperoxide is prepared and used as a solution in ethylbenzene by the air oxidation of ethylbenzene at a temperature between about 120° C. and about 150° C. A yield of up to about 25 percent ethylbenzene hydroperoxide can be obtained in the unoxidized ethylbenzene, which functions as a solvent and more concentrated solutions can be obtained, if desired, by distilling off a portion of the ethylbenzene.

The reaction of ethylbenzene hydroperoxide with ethylene is carried out in a homogeneous, single-phase reaction. When the relatively unstable ethylbenzene hydroperoxide is utilized in a heterogeneous, two-phase reaction, a substantial portion of the ethylbenzene hydroperoxide decomposes in the nonreacting phase. Therefore, we have determined that a homogeneous reaction system is essential for high selectivity. Since ethylbenzene hydroperoxide is not significantly soluble in water, a nonaqueous reaction medium must be used to obtain a homogeneous reaction system. Since the osmium tetroxide catalyst as well as ethylbenzene hydroperoxide and the tetraalkylammonium hydroxide are soluble in many organic polar solvents, an organic polar solvent is used in combination with the ethylbenzene solvent for this homogeneous reaction.

If the reaction of ethylene with ethylbenzene hydroperoxide is carried out under anhydrous conditions, 1-phenylethanol, acetophenone and ethylene glycol are produced in equimolar amounts according to the following equation:

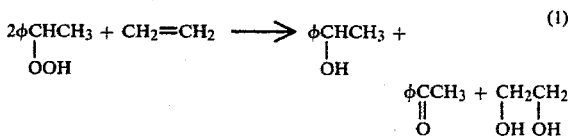

(1)

If water, which is slightly soluble in the solution, is present in the reaction vessel, it will enter into the reaction according to the following equation:

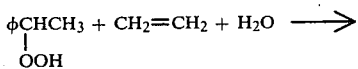
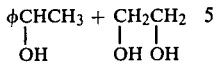 (2)

Since in actual practice both reactions take place when water is present, the selectivity to ethylene glycol based on the ethylbenzene hydroperoxide can be adjusted to some extent by controlling the amount of water present in the reactor.

This reaction is carried out in the presence of a catalytic amount of osmium tetroxide using a polar solvent to ensure a homogeneous reaction since the osmium tetroxide is soluble in the polar solvent. Also present as a solvent is the unoxidized ethylbenzene which is introduced as the predominant component in the ethylbenzene hydroperoxide solution. The reaction solution is maintained strongly alkaline by the presence of a tetraalkylammonium hydroxide which is dissolved therein.

The polar solvent can be an aliphatic or aromatic alcohol having from one to about ten carbon atoms, an aliphatic or aromatic ketone having from three to about ten carbon atoms, an aliphatic or alicyclic ether having from two to about ten carbon atoms, a glycol having from two to about ten carbon atoms, a N,N-dialkyl amide having from three to about ten carbon atoms, an aliphatic or aromatic sulfoxide having from two to about fourteen carbon atoms, an aliphatic or aromatic sulfone having from two to about fourteen carbon atoms, and the like. Examples of suitable polar solvents include methanol, ethanol, propanol, butanol, hexanol, decanol, benzyl alcohol, acetone, methylethyl ketone, methylbutyl ketone, acetophenone, ethylene glycol, propylene glycol, diethylene glycol, tetraethylene glycol, dimethyl formamide, diethyl formamide, dimethyl acetamide, dimethyl sulfoxide, diethyl sulfoxide, di-n-butyl sulfoxide, diphenyl sulfoxide, dibenzyl sulfoxide, dimethyl sulfone, diethyl sulfone, tetramethylene sulfone, diphenyl sulfone, acetonitrile, pyridine, dioxane, tetrahydrofuran, tetrahydropyran, dioxolane, and the like. The amount of polar solvent can be between about 30 and about 98 weight percent of the reaction mixture, but will preferably comprise between about 50 and 80 percent of the reaction mixture.

The amount of ethylbenzene hydroperoxide used in the reaction is not critical but will generally be from about one percent to about 20 weight percent of the reaction system, preferably from about five percent to about 20 percent of the reaction mixture. The amount of ethylbenzene in the reaction system can vary between about 2.5 percent and about 50 weight percent but at preferred conditions of operation it will comprise between about ten and about 30 weight percent of the reaction mixture.

Since ethylene is a gas, it is incorporated into the reaction solution by pressuring the reactor with ethylene. The pressure is not critical, rather it determines the amount of ethylene that is present in the reaction solution and therefore affects the rate of reaction. We find that a pressure between about 25 and about 1,500 psig. is useful, however, we prefer to operate within a pressure range of between about 50 and about 150 psig. as providing a suitable reaction rate without requiring high pressure equipment. The reaction is preferably carried out with a stoichiometric excess of ethylene to substantially completely react all of the ethylbenzene hydroperoxide in the reaction mixture, and more preferably at least about a 25 percent stoichiometric excess of the ethylene.

The catalyst osmium tetroxide is used in catalytic quantities. We find that from 0.01 to ten mmols of the catalyst per 100 ml. of the reaction solution is suitable, however, we prefer to carry out the reaction using from about 0.03 to about 0.1 mmol of catalyst per 100 ml. of the reaction solution. The amount of catalyst can also be related to the amount of osmium metal that is used. Thus, about 50 to about 1,000 ppm. osmium can be used based on the total solution in the reaction vessel, preferably about 100 to about 500 ppm. osmium. Also included in the term osmium tetroxide as used herein including the claims are osmium compounds which are converted to osmium tetroxide by ethylbenzene hydroperoxide including potassium osmate, sodium osmate, lithium osmate, and the like.

A small amount of a tetraalkylammonium hydroxide is also present in the reaction solution, sufficient in amount to maintain the reaction solution at a pH of about 14. This tetraalkylammonium hydroxide serves in this reaction system both as a base and as a phase transfer agent and as such it increases the solubility of ethylene in the reaction liquid. Therefore, the tetraalkylammonium hydroxide aided by its basic properties serves to increase the reaction rate, increase the selectivity to desired products and improve the overall efficiency of the reaction.

The useful tetraalkylammonium hydroxides include those containing lower alkyl groups having from one to about five carbon atoms such as tetramethylammonium hydroxide, tetra-n-butylammonium hydroxide, and the like. This base is used in an amount between about 0.1 and about five weight percent of the reaction solution and preferably within the range of about 0.2 to about two weight percent. The water for reaction, if reaction under equation (2) is desired, can be conveniently supplied as an aqueous solution of the base. This water for reaction can be used in an amount up to about 20 weight percent of the reaction solution, but generally it is used in an amount of between about one and about ten percent such that separation into an aqueous phase and an organic phase is avoided.

The hydroxylation reaction is carried out at a moderate temperature. At higher temperatures the reaction rate increases substantially but this occurs at a significant reduction in selectivity to ethylene glycol. At very low temperatures the selectivity to ethylene glycol is excellent but the reaction rate is slow. Within those constraints we find that a reaction temperature between about −10° C. to about 30° C. is particularly suitable but we prefer to operate within the range of about −10° C. to about 25° C.

This hydroxylation can be performed as a batch reaction, as a continuous reaction or as a semi-continuous reaction. In the batch reaction all the necessary components are placed in a reaction vessel and the reaction is allowed to proceed for about one to about 24 hours for substantially complete reaction of the ethylbenzene hydroperoxide. In the continuous process the components can be introduced into the inlet of an elongated reactor at a rate that substantially complete reaction will have taken place by the time the reaction solution reaches the reactor outlet. The reaction can also be carried out in a semi-continuous manner by metering the reaction components into the first of one or more tank reactors in series.

The reaction product, after removal of unreacted ethylene, is a solution of product ethylene glycol, 1-phenylethanol and acetophenone and also the polar solvent ethylbenzene, tetraalkylammonium hydroxide, osmium tetroxide and water, if added. Since the reaction is generally carried out under conditions, including a stoichiometric excess of ethylene for complete reaction of the ethylbenzene hydroperoxide, there is no significant amount of hydroperoxide in the reaction product. If unreacted ethylbenzene hydroperoxide shows up in the reaction product, it is removed by the use of a suitable reducing agent in an extra processing step as a safety precaution to avoid possible hazards resulting from the undesired decomposition of the hydroperoxide during product work-up. Therefore, insuring the substantial absence of ethylbenzene hydroperoxide in the reaction product represents a safety precaution and avoids substantial processing costs.

The reaction product has been analyzed for oxidation products of ethylene other than ethylene glycol including acetaldehyde, acetic acid, ethanol, acetals of acetaldehyde, glycolaldehyde and glycolic acid and none has been found. The volatile components are distilled out of the reaction mixture into various fractions leaving the osmium tetroxide in the still. Ethylene glycol is separated from the high boiling distillate leaving a mixture of 1-phenylethanol and acetophenone from which the ethylbenzene can be regenerated by a suitable hydrogenation procedure.

DESCRIPTION OF PREFERRED EMBODIMENTS

In the following examples the ethylbenzene hydroperoxide was analyzed by iodometric titration. Ethylene glycol analysis was carried out by gas chromatography and mass spectroscopic analysis. The pH of the solution was determined with a pH meter.

EXAMPLE 1

Example III of U.S. Pat. No. 4,049,724 discloses the preparation of propylene glycol using tert-butyl hydroperoxide in a buffered, aqueous solution at a selectivity of 45 percent based on the hydroperoxide. This experiment was repeated as follows except that ethylbenzene hydroperoxide was used in place of the tert-butyl hydroperoxide.

A 300 ml. thick-walled glass reactor equipped with a stirring magnet was charged with 18.5 g. of water, 1.0 g. $Na_2CO_3$, 1.2 g. $NaHCO_3$ and 0.2 mmol of osmium tetroxide. A measured 33 g. portion of propylene and 71.5 g. of 19 percent ethylbenzene hydroperoxide (98 mmols) were charged into the reactor. The reaction mixture was stirred at ambient temperature (20°-25° C.) for two hours. The pH of the solution was 9.2. The reaction temperature rose from 25° C. to 45° C. and then slowly dropped back to 25° C. The stirring was continued for an additional 30 minutes to ensure complete reaction of the hydroperoxide. Analysis of the reaction product disclosed the production of 0.17 g. (2.24 mmols) of propylene glycol which was a selectivity of 2.3 percent based on the ethylbenzene hydroperoxide.

EXAMPLE 2

In this experiment the reaction of 1-decene and tert-butyl hydroperoxide is carried out by the procedure described in the Sharpless et al report.

In a 500 ml. round bottom flask was placed 200 ml. tert-butyl alcohol, 15 ml. of 10 percent aqueous tetraethylammonium hydroxide (about 10 mmols) and 19 ml. (14 g., 100 mmols) 1-decene. The solution was cooled to <0° C. in an ice-salt bath with stirring. Then 23 ml. of 70 percent tert-butyl hydroperoxide were added (160 mmols), followed by 10 ml. of 0.5 percent osmium tetroxide in tert-butyl alcohol (about 0.2 mmol). The solution became purple in color. This was stirred for two hours at 0° C.

After refrigerating the flask at about 3° C., it was observed to have a pale yellow color. Thereupon, 100 ml. of 5 percent by weight $NaHSO_3$ in $H_2O$ were added. The color became a murky purple which gradually became pale pink with stirring and warming to room temperature. The flask was then placed in a rotary evaporator and the tert-butyl alcohol and $H_2O$ were removed. A pasty yellow jelly remained. This was taken up in 100 ml. of ether, in which it dissolved quite readily. The ether solution was transferred to a separatory funnel and washed with several 200 ml. portions of saturated brine solutions. The final washing was made and the layers separated. The organic layer was dried with $MgSO_4$, filtered, and the ether evaporated on a rotary evaporator. There seemed to be some solid suspended, so the material was filtered, ether added, and the evaporation continued at 70° C. A 15.82 g. liquid product was obtained. Gas-liquid chromatographic analysis showed it to be 81.8 weight percent diol. This represents a 74.4 percent selectivity based on 1-decene compared with a 73 percent selectivity reported by Sharpless et al and verifies that the Sharpless et al experiment was accurately duplicated. This data also represents a 46.5 percent selectivity based on the tert-butyl hydroperoxide.

EXAMPLE 3

This experiment demonstrates that the process of Example 2 is not useful with ethylbenzene hydroperoxide.

A 14 g. (100 mmols) sample of 1-decene, 200 ml. of t-butanol and 15 ml. of ten percent aqueous tetraethylammonium hydroxide were added to a 500 ml. round bottom flask. The flask and contents were cooled to 0° C. in a sodium chloride ice bath. After reaching temperature, 113 g. of 20 percent (160 mmols) ethylbenzene hydroperoxide and ten ml. of 0.5 percent osmium tetroxide in t-butanol were added. The reaction was allowed to proceed for about 15 hours. Analysis after product recovery showed that the reaction with ethylbenzene hydroperoxide had formed 4.32 g. (24.8 mmols) of 1,2-dihydroxydecane, a 15.5 percent selectivity based on the ethylbenzene hydroperoxide. This also represents a 24.8 percent selectivity to the diol based on the 1-decene, which had completely reacted.

The following experiments demonstrate the effectiveness of the reaction of ethylene with ethylbenzene hydroperoxide.

EXAMPLE 4

A charge of 100 ml. of t-butanol and 7.5 ml. of ten percent aqueous tetraethylammonium hydroxide was placed in a 300 ml. thick-walled glass reactor equipped with a thermocouple and a stirring magnet. The solution was cooled to 0° C. in an ice-salt bath. After adding 59 g. of 20 percent ethylbenzene hydroperoxide (80 mmols) to the chilled solution, the reactor was sealed. Ethylene was introduced into the reactor to a pressure of about 120 psi. Then 5 ml. of 0.5 percent osmium tetroxide (0.1 mmol) in t-butanol was pressured into the reactor in a stream of ethylene. The ethylene pressure was adjusted to 150 psi. The total amount of ethylene that was charged to the reactor, as measured by a calibrated rotameter, was 274 mmols. The reaction was allowed to proceed for six hours at 0° C. and at about 150 psi. (1.03 MPa). The reactor was then permitted to stand overnight at room temperature. The ethylene vented at the conclusion of the hydroxylation reaction amounted to 210 mmols according to measurement in a wet-gas meter. Iodometric titration of the reaction solution gave zero percent ethylbenzene hydroperoxide. After evaporating the product, 100 ml. of ethanol were added to precipitate the inorganic portion. Analysis of the evaporated filtrate showed 3.57 g. of ethylene glycol (58 mmols) which is a selectivity of 72.5 percent based on the ethylbenzene hydroperoxide as determined by equation (2) above.

The selectivity of ethylene to ethylene glycol based on the 58 mmols of product ethylene glycol and the 64 mmols of unrecovered ethylene was calculated as 90 percent. But further analysis was carried out to account for possible handling losses of ethylene. An identical blank test was run except that no ethylbenzene hydroperoxide and no catalyst were used. This resulted in a 95 percent recovery of ethylene. The five percent difference is believed to be the ethylene handling losses including ethylene dissolved in the solution. It was concluded that the selectivity of ethylene to ethylene glycol based on reacted ethylene is at least about 95 percent.

EXAMPLE 5

The reaction procedures, conditions and quantities of Example 4 were repeated except that the amount of ethylene charged to the reactor was not measured. The low boiling fraction in the evaporated filtrate following the precipitation of the inorganic portion was analyzed for two-carbon oxygenated derivatives of ethylene. A combination of gas chromatographic and mass spectrographic analysis disclosed none of the following in the product: acetaldehyde, acetic acid, ethanol, acetals of acetaldehyde, glycolaldehyde and glycolic acid. The sensitivity of this combined analysis was estimated to be about 0.5 weight percent of the total product.

EXAMPLES 6–9

Example 5 was repeated in a series of experiments except that the concentration of tetraethylammonium hydroxide in water was varied to determine the effect of the amount of base on the production of ethylene glycol. Each solution was found to have a pH of 14. The results are set out in Table I.

TABLE 1

| Ex. | Base amount, ml. | conc. % | Ethylene glycol.g. |
|---|---|---|---|
| 6 | 7.5 | 5 | 3.0 |
| 7 | 7.5 | 10 | 3.5 |
| 8 | 7.5 | 25 | 1.95 |
| 9 | 19 | 10 | 2.9 |

EXAMPLES 10 and 11

The procedures of Example 5 were duplicated except that the base was varied to determine the effect of base type on the yield of ethylene glycol. The pH measured 14 in each solution. These results are set out in Table II.

TABLE II

| Ex. | Base | Amount, ml. | Conc. % | Ethylene glycol, g. |
|---|---|---|---|---|
| 7 | $(CH_3CH_2)_4NOH$ | 7.5 | 10 | 3.52 |
| 10 | $(CH_3CH_2CH_2CH_2)_4NOH$ | 7.5 | 10 | 3.36 |
| 11 | $(CH_3)_4NOH$ | 7.5 | 10 | 2.96 |

EXAMPLES 12–14

The details of Example 5 were repeated except that two reaction cycles were used in which the reaction temperature and/or reaction time were varied to determine the effect of these variables on the yield of ethylene glycol. The results are shown in Table III.

TABLE III

| Ex. | First Cycle Temp. °C. | Time, hrs. | Second Cycle Temp. °C. | Time, hrs. | Ethylene glycol, g. |
|---|---|---|---|---|---|
| 7 | 0 | 6 | 25 | 16 | 3.52 |
| 12 | −10 | 1 | 25 | 5 | 3.13 |
| 13 | 0 | 1 | 25 | 5 | 2.91 |
| 14 | 25 | 6 | — | — | 2.44 |

EXAMPLES 15–19

The procedures of Example 5 were repeated in that 100 ml. of various solvents were used. The results are set out in Table IV.

TABLE IV

| Ex. | Solvent | Ethylene glycol, g. |
|---|---|---|
| 7 | t-butanol | 3.52 |
| 15 | diethylene glycol | 3.26 |
| 16 | propylene glycol | 3.42 |
| 17 | p-dioxane | 3.96 |
| 18 | ethylene glycol monobutylether | 2.91 |
| 19 | ethylene glycol monomethylether | 2.98 |

EXAMPLES 20–23

The amount of catalyst was varied in a series of runs otherwise carried out as described in Example 5. These solutions were all found to have a pH of 14. The variations in ethylene glycol produced is recorded in Table V (0.1 mmol $OsO_4$ is about 250 ppm.).

TABLE V

| Ex. | $OsO_4$, mmol | Ethylene glycol, g. |
|---|---|---|
| 20 | 1.0 | 3.82 |
| 7 | 0.1 | 3.52 |
| 21 | 0.05 | 2.67 |
| 22 | 0.035 | 2.11 |
| 23 | 0.020 | 0.33 |

It is to be understood that the above disclosure is by way of specific example and that numerous modifications and variations are available to those of ordinary skill in the art without departing from the true spirit and scope of the invention.

We claim:

1. A method of preparing ethylene glycol in a homogeneous, single-phase reaction which comprises contacting ethylbenzene hydroperoxide with an excess of ethylene at a pressure of between about 25 and about 1,500 psig. in a solution comprising between about 2.5 and about 50 weight percent ethylbenzene, between about one and about 20 weight percent ethylbenzene, hydroperoxide and between about 30 and about 98 weight percent of an organic polar solvent in the presence of a sufficient amount of a tetraalkylammonium hydroxide in which the alkyl group has from one to about five carbon atoms to give a pH of about 14 and a catalytic amount of osmium tetroxide at a moderate temperature.

2. A method of preparing ethylene glycol in accordance with claim 1 in which there is up to about twenty percent water.

3. A method of preparing ethylene glycol in accordance with claim 2 in which the polar solvent is selected from aliphatic alcohols, aliphatic ketones and aliphatic ethers having up to about six carbon atoms.

4. A method of preparing ethylene glycol in accordance with claim 2 in which there is about 100 to about 500 ppm. osmium as the metal based on the reaction solution.

5. A method of preparing ethylene glycol in accordance with claim 2 in which there is about 0.1 to about five weight percent of the tetraalkylammonium hydroxide.

6. A method of preparing ethylene glycol in accordance with claim 2 in which the temperature is between about $-10°$ C. and about $30°$ C.

7. A method of preparing ethylene glycol in accordance with claim 1 in which there is at least about a 25 percent stoichiometric excess of ethylene.

8. A method of preparing ethylene glycol in accordance with claim 2 in which there is at least about a 25 percent stoichiometric excess of ethylene.

* * * * *